United States Patent
Masoud et al.

(10) Patent No.: US 9,723,433 B2
(45) Date of Patent: Aug. 1, 2017

(54) SYSTEMS AND METHODS FOR WIRELESS COMMUNICATION WITH IMPLANTABLE AND BODY WORN DEVICES

(71) Applicant: SORIN CRM SAS, Clamart (FR)

(72) Inventors: Javaid Masoud, Shoreview, MN (US); David Amaoua, Versailles (FR)

(73) Assignee: SORIN CRM SAS, Clamart (FR)

( * ) Notice: Subject to any disclaimer, the term of this patent is extended or adjusted under 35 U.S.C. 154(b) by 0 days.

(21) Appl. No.: 15/148,514

(22) Filed: May 6, 2016

(65) Prior Publication Data

US 2016/0330573 A1    Nov. 10, 2016

(30) Foreign Application Priority Data

May 7, 2015   (EP) ..................... 15166692

(51) Int. Cl.
*H04B 7/00*   (2006.01)
*H04W 4/00*   (2009.01)
(Continued)

(52) U.S. Cl.
CPC ........... *H04W 4/008* (2013.01); *A61B 5/0024* (2013.01); *A61N 1/37217* (2013.01); *A61N 1/37252* (2013.01); *G06F 19/3418* (2013.01); *G06F 21/30* (2013.01); *G06F 21/44* (2013.01); *H04W 4/22* (2013.01); *G06F 19/322* (2013.01);
(Continued)

(58) Field of Classification Search
CPC ..... H04W 84/18; H04W 76/02; H04W 88/06; H04M 1/7253; H04M 2250/02; A61B 5/0012; A61B 5/0031; A61B 5/021; A61B 5/0024; G06F 19/3418; G06F 21/30; G06F 21/44; G06Q 50/22; A61N 1/37217; A61N 1/37252

USPC ............ 455/41.1, 41.2, 422.1, 550.1, 575.1, 455/575.6; 340/539.12
See application file for complete search history.

(56) References Cited

U.S. PATENT DOCUMENTS

| | | | |
|---|---|---|---|
| 2012/0007712 A1* | 1/2012 | Tung ..................... | B60R 25/243 340/5.72 |
| 2014/0229385 A1* | 8/2014 | Neafsey ............. | G06Q 20/3674 705/67 |
| 2014/0273824 A1* | 9/2014 | Fenner ................. | H04B 5/0031 455/41.1 |

OTHER PUBLICATIONS

Bluetooth, Medical Devices WG: "Health Device Profile", Bluetooth Doc, Jun. 26, 2008, Retrieved from the Internet at https://www.bluetooth.org/docman/handlers/DownloadDoc.ashx?doc_id=260864&vid=290095&_ga=1.128761092.961309788.1447059724 on May 5, 2016, 44 pages.

(Continued)

*Primary Examiner* — Nhan Le
(74) *Attorney, Agent, or Firm* — Foley & Lardner LLP

(57) ABSTRACT

A medical monitoring and communication system for wireless communication between an implantable medical device, a mobile user device, and a remote server includes a sensor device coupled to the implantable medical device. The sensor device is configured to default to a master mode prior to pairing with the mobile user device, listen for a request to connect from the mobile user device, refrain from communicating with the mobile user device responsive to the request to connect from the mobile user device being invalid, and switch to a slave mode to allow cooperative pairing with the mobile user device responsive to the request to connect from the mobile user device being valid. The mobile user device facilitates communication between the sensor device and the remote server when the mobile user device and the sensor device are cooperatively paired.

18 Claims, 9 Drawing Sheets

(51) Int. Cl.
  *H04W 4/22*    (2009.01)
  *A61N 1/372*   (2006.01)
  *A61B 5/00*    (2006.01)
  *G06F 19/00*   (2011.01)
  *G06F 21/30*   (2013.01)
  *G06F 21/44*   (2013.01)
  *H04W 12/04*   (2009.01)
  *H04W 12/06*   (2009.01)
  *H04W 88/04*   (2009.01)
  *H04W 84/20*   (2009.01)

(52) U.S. Cl.
  CPC .. *G06F 19/3481* (2013.01); *G06F 2221/2103* (2013.01); *H04W 12/04* (2013.01); *H04W 12/06* (2013.01); *H04W 84/20* (2013.01); *H04W 88/04* (2013.01)

(56) References Cited

OTHER PUBLICATIONS

Lake, et al. Internet of Things: Architectural Framework for eHealth Security, Journal of ICT, Jan. 1, 2014, Retrieved from the Internet at http://riverpublishers.com/journal/journal_articles/RP_Journal_2245-800X_133.pdf on May 5, 2016, 28 pages.
Preliminary Search Report for European Patent Application No. 15166692.2, dated Nov. 9, 2015, 7 pages.
Sulaiman, et al. A Security Architecture for e-Health Services, 10th International Conference on Advanced Communication Technology, IEEE, Feb. 17, 2008, 6 pages.

* cited by examiner

SYSTEMS AND METHODS FOR WIRELESS COMMUNICATION WITH IMPLANTABLE AND BODY WORN DEVICES

CROSS-REFERENCE TO RELATED PATENT APPLICATIONS

This application claims the benefit of and priority to European Patent Application No. 15166692, filed May 7, 2015, which is incorporated herein by reference in its entirety.

BACKGROUND

Communication with implantable devices such as pacemakers, defibrillators, and other devices is traditionally done by custom designed instruments known as a programmer, a patient companion, or a patient monitor. These programmers are typically used in an operating room when a patient is receiving an implantable device to insure proper device settings and to check the implant functionality. The cost to build these units is often significantly high and requires specialized trained staff to operate and maintain them. Also, these programmers are often bulky, heavy, and difficult to move from one location to other. Further, the capability provided by these programmers is often limited to the software designed for a particular implant, thus these programmers often lack the capability to connect to a hospital infrastructure or an external environment.

Not long after these units are released their components become dated due to advancements in hardware and software technologies in the computer industry. In order to maintain them for a period of time and to recover the development cost poses a significant challenge.

A home monitor may be provided to a patient for use in the patient's home. Home monitors are configured to receive alerts from the implantable medical device and can immediately notify the health care professional of the patient's condition. Home monitors may also be expensive to build, while often being provided free to patients. The functionality of home monitors is often limited, requiring a continuous power source (e.g., a wall plug-in, etc.) with a limited communication range. Home monitors do not provide patients with the option of mobility, requiring patients to stay within a limited area.

SUMMARY

One embodiment relates to a medical monitoring and communication system for wireless communication between an implantable medical device, a mobile user device, and a remote server. The medical monitoring and communication system includes a sensor device communicably coupled to the implantable medical device. The sensor device is configured to default to a master mode prior to pairing with the mobile user device, listen for a request to connect from the mobile user device, refrain from communicating with the mobile user device responsive to the request to connect from the mobile user device being invalid, and switch to a slave mode to allow cooperative pairing with the mobile user device responsive to the request to connect from the mobile user device being valid. The mobile user device facilitates communication between the sensor device and the remote server when the mobile user device and the sensor device are cooperatively paired.

Another embodiment relates to a method for wireless communication between an implantable medical device, a mobile user device, and a remote server. The method includes providing a sensor device communicably coupled to the implantable medical device; setting the sensor device to default to a master mode when not paired with a mobile user device; receiving, by the sensor device, a connection request from the mobile user device; determining, by the sensor device, whether the connection request is a valid request; refraining, by the sensor device, from communicating with the mobile user device responsive to the connection request being invalid; and switching, by the sensor device, to a slave mode and cooperatively pairing the mobile user device and the sensor device responsive to the connection request being valid.

Another embodiment relates to a method for authenticating a connection for the transfer of encrypted data from a sensor device to a user device. The method includes providing, by a user device, user credentials to a remote server; receiving, by the user device from the remote server, a connection secret associated with the user credentials; comparing, by a sensor device, the connection secret to a connection secret stored within a memory of the sensor device; generating, by the sensor device and the user device, an encryption key responsive to the comparison indicating a valid connection secret; and establishing a secure connection between the user device and the sensor device using the encryption key.

Another embodiment relates to a method for remote analysis of data acquired by a sensor device. The method includes acquiring, by a sensor device, sensor data including at least one of physiological data regarding a user of the sensor device and device data regarding the sensor device; encrypting, by the sensor device, the sensor data with two layer of encryption; receiving, by a user device communicably coupled to the sensor device, the sensor data; performing, by the user device, a first decryption on the sensor data using a first key; transmitting, by the user device, the sensor data to a remote server; performing, by the remote server, a second decryption on the sensor data using a second key; analyzing, by the remote server, the sensor data; and sending, by the remote server, a summary of the sensor data to the user device.

BRIEF DESCRIPTION OF THE DRAWINGS

Further features, characteristics and advantages of the present invention will become apparent to a person of ordinary skill in the art from the following detailed description of preferred embodiments of the present invention, made with reference to the drawings annexed, in which like reference characters refer to like elements, and in which.

DETAILED DESCRIPTION

Figure 1:
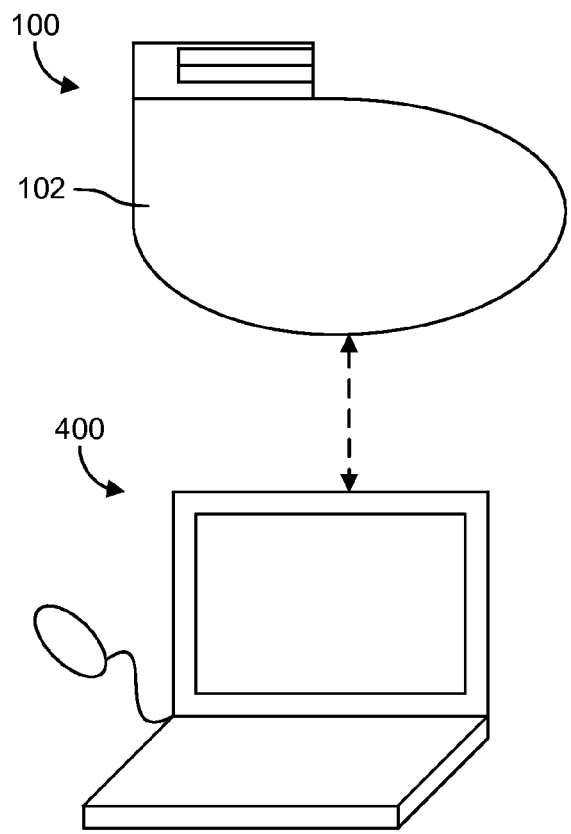
FIG. 1 is an illustration of a sensor device and a programmer device, according to an exemplary embodiment.

Referring to the Figures generally, the present disclosure relates to systems and methods for wireless communication with implantable devices (e.g., implantable medical devices, pacemakers, defibrillators, etc.) and/or body worn devices (e.g., heart rate monitors, smart watches, smart bands, pedometers, etc.). More specifically, the present disclosures relates to systems and methods for secure communication between mobile computing devices (e.g., smartphones, tablets, smart watches, laptops, etc.) with implantable medical devices and/or body worn devices using communication protocol such as Bluetooth Low Energy communication. The secure communication may include a double secure encryption mechanism to protect both data exported from the implantable and/or body worn device(s) and the connection to the implantable and/or body worn device(s).

As medical device technologies evolve, different types of implantable devices are used to treat various types of diseases. For example, slow heart rate conditions or missing heart beat conditions may be treated by pacemakers, and arrhythmic (fast) rate may be treated by defibrillators to restore a heart rate of a user to a normal state by delivering a fast pacing therapy or delivering a high shock. As another example, there are other types of implantable devices which may be used to treat neurological conditions such as obesity, Parkinson's, diabetes, etc. Other devices may also be used to collect physiological & diagnostic data, such as an implantable loop recorder and various other types of sensors that may be positioned around the body to monitor a user for heart rate variability, blood pressure, weight, etc.

Currently, the systems and methods being implemented to communicate with implantable medical devices include various technical problems. First, communication with an implant is based on a proprietary communication protocol which is developed by each implantable device manufacturer independently. The volume of implantable devices produced is therefore limited and the unitary cost is high compared to similar technology available in the consumer market. Additionally, proprietary systems do not allow seamless integration of data from other sensors (implanted or body worn) without introducing additional hardware components; therefore it limits the ability to treat patients in a more holistic manner. Another technical problem is that the hardware and protocol implementation has been left to the discretion of the device manufacturer. This prevents the interoperability of the implant with any hardware. Actually, each implantable device manufacturer designs, produces, and distributes its own equipment to communicate with the implantable device. Still another technical problem relates to the lack of interconnectivity between medical devices, both implanted and worn. For example, a number of sensors related to health monitoring and communication, implanted as well as external, are being developed and used by patients; however the data gathered by each individual device is not interconnected. The need to make interconnected sensor systems that communicate in a secure manner may bring new ways to provide meaningful information to healthcare providers and the patients, as well as feeding sensor-embedded algorithms to facilitate adaptive therapy based on the data received from various sensors. Yet another technical problem is that security mechanisms implemented in standard wireless protocols, such as Bluetooth or Wi-Fi, have been compromised. Therefore, medical manufacturers need to meet patient safety requirements.

Instead of using custom built equipment, consumer technologies with wireless receivers/transmitters (e.g., smartphones, tablets, laptops, etc.), which are substantially more cost effective, may be used. These technologies may be used to communicate with implantable devices and various body worn devices to retrieve physiological and diagnostic data, and transmit the data to a remote server in a secure manner for processing. The communication technology may be power efficient, highly reliable, and provide data security during communication with implantable devices and other sensors. Once the data is processed by the remote server, the information regarding patient's condition may then be sent to healthcare providers, patients, caregivers, and the like such that they may view the information to monitor the patient's health/status and take appropriate actions to treat the patient if needed.

The communication system may be secured through a multi-tiered approach; an activator (i.e., programmer, etc.) is used to activate an implant (or body worn device) upon which it scans for an external instrument. During this phase, the implant may act as a master device in a paring process. When the implant hears from an instrument (e.g., portable device, etc.), it switches from a scanning mode to an advertising mode which allows the instrument to find the implant to open a communication session. The implant then enters into a slave mode and the instrument behaves as the master device for the duration of the session. The instrument may then receive data from the implant which is then transmitted wirelessly (e.g., via a cellular network, the Internet, Wi-Fi, etc.) to a remote server. Therefore, the proposed systems and methods facilitate the remote monitoring of a patient with an implanted medical device and communication between a mobile user device, an implanted medical device, and/or a remote server.

The sensing, monitoring, and communication system may be able to collect data from multiple sensor devices. The system may include multiple implants (e.g., a pacemaker, a defibrillator, a neurological sensor, etc.), multiple non-implanted sensors (e.g., a weight scale, a blood pressure sensor, an activity sensor, an oxygen saturation sensor, etc.), and multiple instruments (e.g., a smartphone, a tablet, a smart watch, a computer, a laptop, etc.). The instruments send the data to a remote server to apply algorithms on the collected data to determine patient's condition (e.g., improving, same, getting worse, etc.) and alert appropriate health care providers accordingly. The algorithms may provide a risk score of patient's condition based on the data analysis. Additional data sensors may be added or removed from the sensing, monitoring, and communication system, based on the patient's needs, in a seamless manner.

One aspect of the present disclosure involves a fully secure medical system. The medical system consists of an implantable medical device, a clinician programmer, a remote server, and any portable/mobile device with computational and/or displaying capabilities. The mobile device may be authenticated through a challenge of secret question/answer exchange between the implant and the mobile device, and between the mobile device and the remote server. The mobile device may also be authenticated by the user of the clinician programmer to receive data from the implant and send the data to the remote server. The mobile device may be authenticated by the implant through a challenge question answer exchange where the implant has unique information about the mobile device and the mobile device has unique information about the implant. The mobile device receives the unique information about the implant from being authenticated by the remote server and/or by the clinician programmer. Part of this information is used to generate a unique key to encrypt and decrypt data between the implant and the mobile device. The implant also knows unique information about the remote server such that any data it transmits is encrypted twice. The mobile device may be able to remove a first layer of decryption, but a second layer is decrypted by the remote server.

In order to make the system fully secure a connection between the implantable medical device and the mobile device is authenticated to restrict non-authorized user from using a non-authorized device to interact with the implantable medical device. Also, sensitive data is encrypted to protect the data from being captured by a non-authorized user. An example implementation of an authentication and encryption process may be as follows.

a) Once the implantable medical device is implanted and prior to the patient being discharged, the implantable medical device is programmed with two "secrets." A first secret used to facilitate the encryption of a wireless link between the implantable medical device and the mobile device, and a second secret used to encrypt the data acquired by the implantable medical device, where the remote server knows the key to decrypt the data.

b) A patient is given personal credentials to connect to the remote server that correspond with the secrets programmed into the implantable medical device.

c) The patient downloads a dedicated app from an app store such as GOOGLE PLAY® for Android® and Apple Store® for iOS®.

d) The patient enters the personal credentials via the mobile device application. In order to protect against an unauthorized access of a patient's mobile device by an unauthorized individual, the personal credentials may not be stored on the mobile device application, and therefore an unauthorized user cannot start communication with the implantable medical device.

e) The mobile device application connects to the remote server using the personal credentials of the user and downloads a secret associated with the first secret of the implantable medical device.

f) The mobile device application starts a paring procedure with the implantable medical device by a connection question derived from the secret which the implantable medical device may be able to validate with the first secret.

g) During the pairing procedure a temporary key is exchanged over the wireless link. The implantable medical device and the mobile device application combine the temporary key with the first secret to build a long term encryption key to encrypt the data exchange over the wireless link between the implantable medical device and the mobile device.

h) Data is acquired by the implantable medical device and is double encrypted with the long term encryption key and the second secret.

i) The data is transferred to the mobile device where a first decryption process is performed to remove the long term encryption key from the data.

j) The data is uploaded to the remote server where the server uses a data key associated with the second secret to perform a second decryption process to decrypt the data.

According to an exemplary embodiment, the users of the system include a patient and a healthcare provider. Healthcare providers may be authenticated through credentials which are used to log into the remote server via the clinician programmer. The clinician programmer is considered a secure device due to its location and limited access to only healthcare providers. In one embodiment, healthcare providers register patients with their implantable medical device by serial number and personal credentials which may be stored on the remote server. A patient with an implantable medical device is entered into the system by the healthcare provider. To authenticate the patient, he/she is given personal credentials to login to the remote server. The system is authenticated with short term and long term keys, and a secret answer to a question which is known by the remote server and the implant.

Another aspect of the present disclosure involves where the implant starts up in a master mode. The implant may be activated through many means (e.g., physical proximity, timer based, etc.) where the implant goes into a slave/listen mode. Once the implant hears from a specific instrument (e.g., a mobile device, a programmer, a patient companion, etc.), it switches its role and responds to the request. This mechanism allows both the implant and the instrument to find each other and authenticate each other prior to establishing a bi-directional communication session. The mechanism described above uniquely address couple of items: (i) it enables secure communication between an implant and a specific instrument (i.e., the implant is not discoverable by any other instrument, non-approved device cannot establish a session with the implant, etc.), (ii) it conserves power in the implant by not constantly transmitting identification information and then listening for responding information followed by validation. The approach described above also applies to any third party device (e.g., a body worn device, etc.) which could become part of the system to collect specific data like blood pressure, activity, weight, and other physiological parameters where the overall system is fully secure.

Yet another aspect of the present disclosure involves a patient personal monitoring and communication system. The patient personal monitoring and communication system includes an implantable device and a mobile computing device having a screen and contains a battery for easy mobility and may be with the patient at any time. The mobile computing device may be configured to provide meaningful feedback to the patient regarding their implant state. The mobile computing device may also act as a hub between the implant and a remote server, where it communicates with the implantable device through a double secure communication protocol.

Still another aspect of the present disclosure involves informing the patient regarding their implant and health condition in a holistic manner. Today patients are unaware of their implant status and data they receive from their weight scale, blood pressure, activity level and other devices is based on daily measurements, but information related to data trending information is unavailable over time. The mobile computing device may communicate with the implant over a secure link and upload implant data to the remote server. Additionally, the mobile computing device may receive a patient's daily physiological data (e.g., blood pressure, activity, heart rate, etc.) and may upload the physiological data securely to the remote server. All the data received by the remote server is decrypted and processed. In one embodiment, the remote server may determine that a patient requires immediate attention and notify the patient, the patient's health care provider, and/or the patient's caregiver based on the processed data. In another embodiment, the mobile computing device may download a summary (e.g., a report, etc.) based on the processed data. The patient may be provided information regarding their daily, weekly, and/or monthly trends based on their physiological data. The patient may be further provided information regarding their implant (e.g., battery level, connection strength, etc.).

Another aspect of the present disclosure relates to body area network consisting of multiple devices. These devices may include implantable devices, body worn device, sensors, devices used periodically to take vital readings, and the like. Each device may communicate with the other device to pass relevant data to each other to better treat a patient. For example, to enable a painless shock a device could inject a medication before a shock is delivered. It could be used to treat heart failure where multiple sensors/devices are monitoring, communicating, and treating different parameters. Each of the devices could contain multiple communication protocol in order to send data to an external central device which acts like a data collector/transport "hub" in the most efficient manner after which data is sent to a remote server through a different communication protocol (e.g., cellular, Wi-Fi, wired, etc.). One central hub device may periodically communicate with multiple devices in the body area network. The hub device may receive data from one device, apply smart algorithm to process the data, and send a command to a second device to take a particular action based on the processed data.

According to the exemplary embodiments shown in FIGS. 1-8B, a system for communication with implantable and/or body worn devices includes a sensor device, shown as sensor device 100; a user device, shown as portable device 200; a server, shown as remote server 300; and a programming device, shown as programmer 400.

Referring to FIG. 1, the sensor device 100 is configured to monitor characteristics of at least one of the sensor device 100 itself and a user of the sensor device 100. By way of example, the characteristics of the user may include, but are not limited to, a heat rate, a blood pressure, a body temperature, an activity level, a respiratory rate, vital signs, and other physiological activity. By way of another example, the characteristics of the sensor device 100 may include, but are not limited to a battery power level, a connection strength (e.g., a wired connection, a wireless connection, etc.), and the like. As shown in FIG. 1, the sensor device 100 is an implantable medical device, shown as implantable medical device 102, configured to be surgically implanted at a desired location of/within a user's body. In another embodiment, the sensor device 100 is or includes a body worn device (e.g., a smart watch, heart rate monitor, pedometer, etc.) configured to be worn by a user (e.g., on a wrist, an ankle, a chest, a head, a waist, etc.) or disposed on a surface (e.g., skin, etc.) of the user's body. In other embodiments, the system includes a combination of implantable medical devices 102 and body worn devices. In some embodiments, the sensor device 100 is configured to facilitate some sort of treatment for the user. For example, the sensor device 100 may monitor the insulin levels of a patient where the sensor device 100 may be commanded (e.g., by the remote server 300 via the portable device 200, etc.) to administer a dosage of insulin (i.e., a treatment, etc.) responsive to the blood sugar level of the user decreasing below a predetermined threshold.

As shown in FIG. 1, the programmer 400 may be communicably coupled to the sensor device 100 and configured to program the sensor device 100 (e.g., with a data secret and a connection secret, etc.) prior to being implanted into a patient or prior to a patient's discharge. In other embodiments, the sensor device 100 is programmed at the time of manufacture. The programmer 400 may be considered a secure device due to its location and limited access to only healthcare providers.

Figure 2:
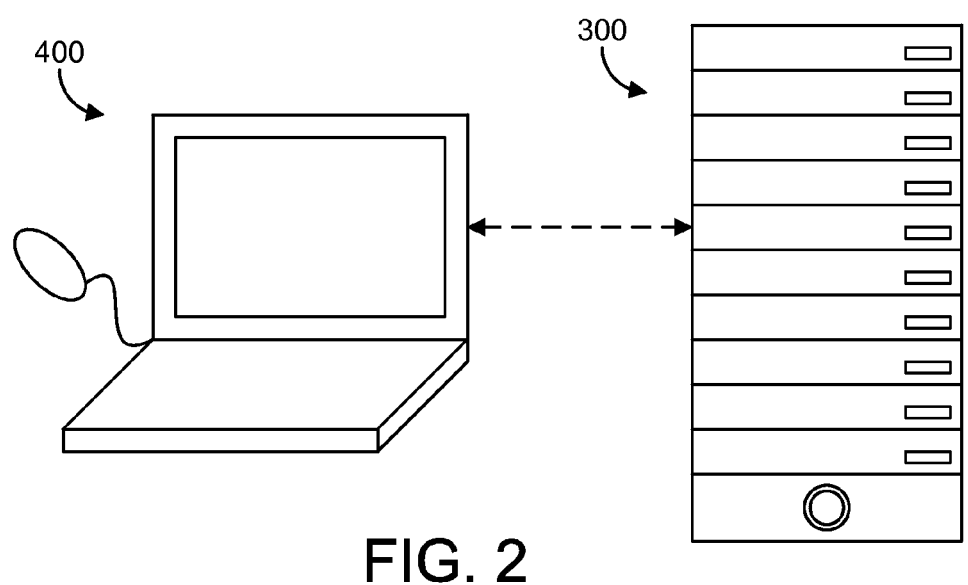
FIG. 2 is an illustration of a remote server and a programmer device, according to an exemplary embodiment.

Referring now to FIG. 2, the programmer 400 may also be communicably coupled to the remote server 300. In some embodiments, the remote server 300 is configured to receive user credential information from the programmer 400. The remote server 300 may be configured to store user credentials for a plurality of users of sensor devices 100. The remote server 300 may also be configured to store data keys and connection secrets that correspond with each of the plurality of sensor devices 100 and user credentials of each user of the sensor device 100 such that the remote server 300 is able to connect with the sensor devices 100 and decrypt data acquired by the sensor device 100.

Figure 3:
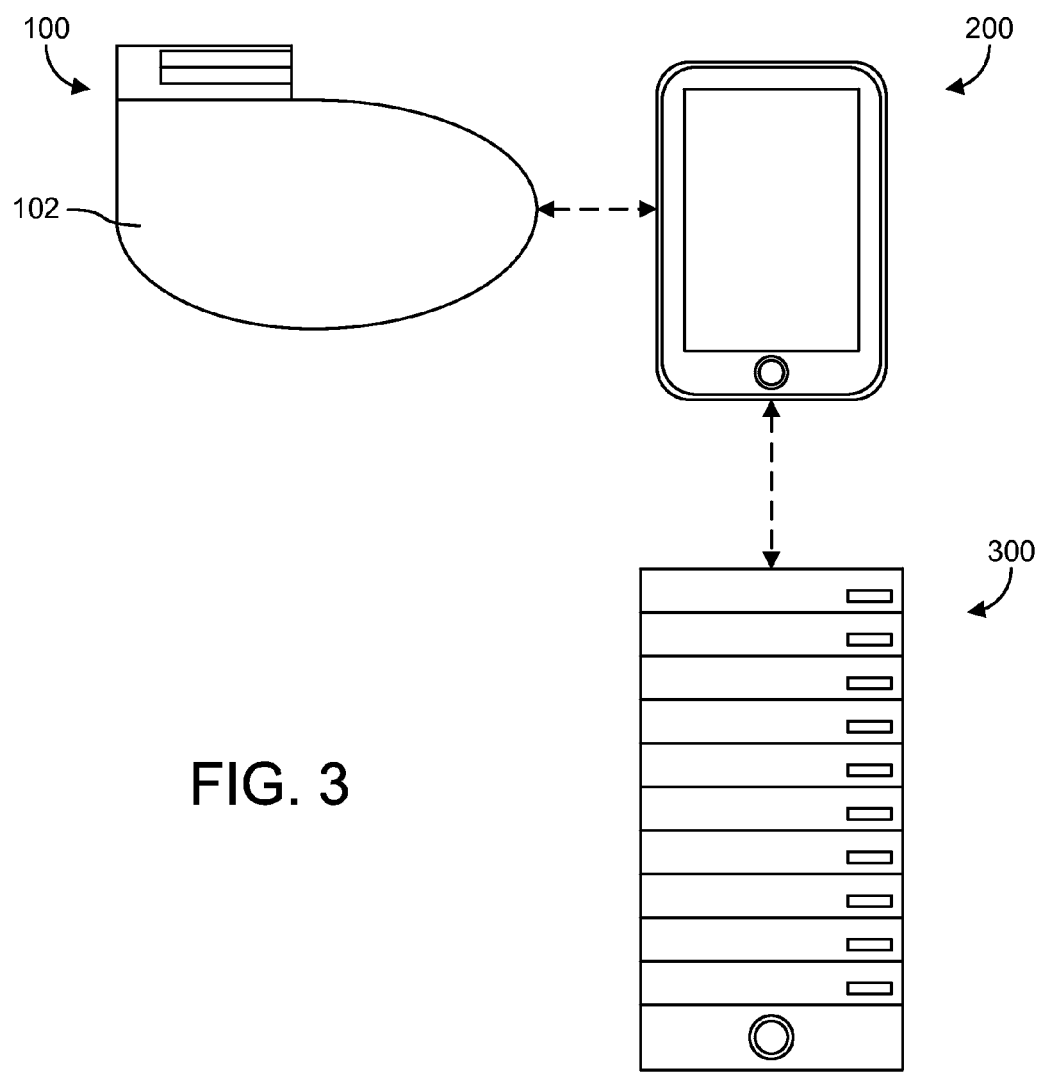
FIG. 3 is an illustration of communication between a sensor device and a remote server via a user device, according to an exemplary embodiment.

Referring now to FIG. 3, the portable device 200 is configured to establish a connection between the sensor device 100 and the remote server 300. The portable device 200 may be configured to send and receive data to/from the sensor device 100 and the remote server 300. In one embodiment, the portable device 200 is a smartphone. In other embodiments, the portable device 200 is another type of portable device (e.g., a tablet, a laptop, a watch, a form factor device, etc.). In an alternative embodiment, the user device is structured as a stationary device (e.g., a desktop computer, etc.).

Figure 4:
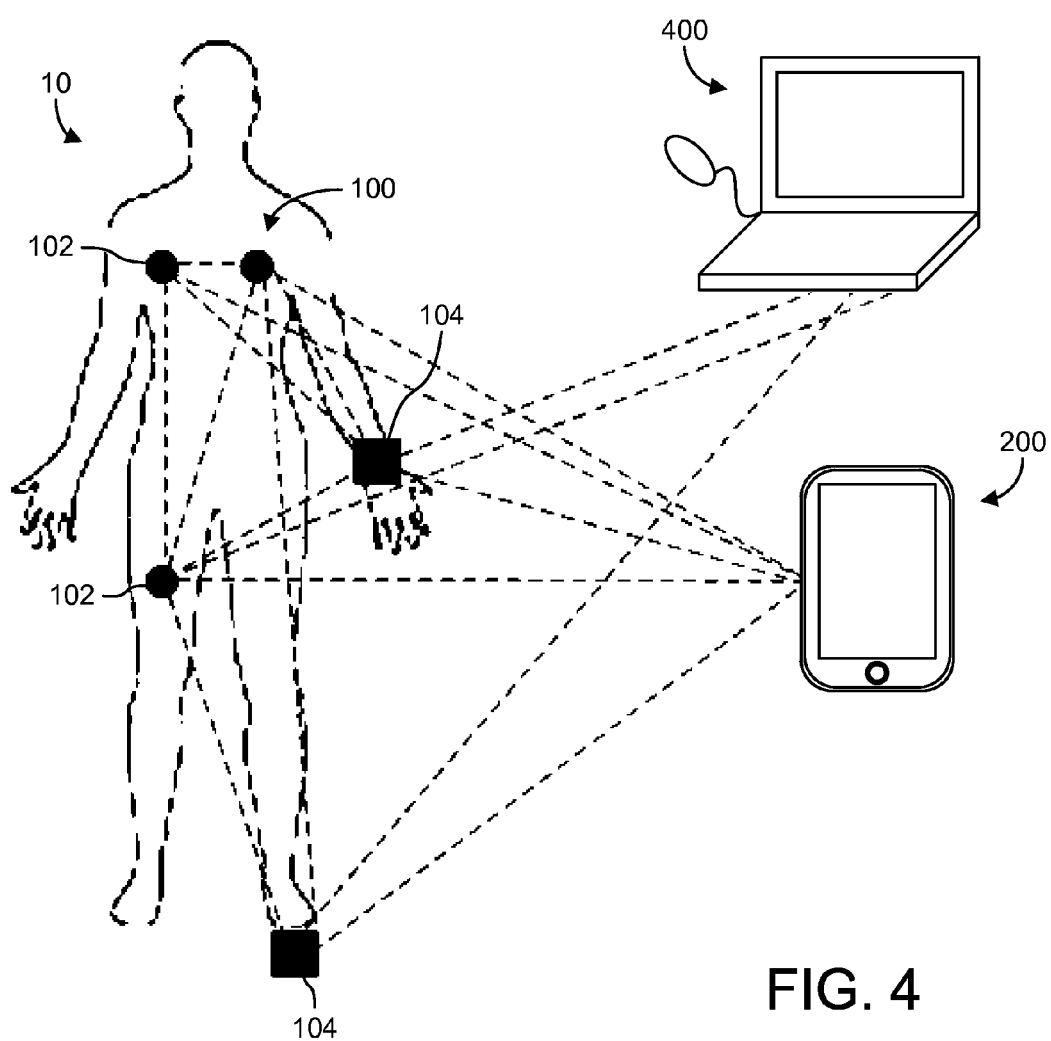
FIG. 4 is an illustration of a body area network, according to an exemplary embodiment.

Referring now to FIG. 4, in some embodiments, the sensor devices 100 form a body area network, shown as body area network 10. As shown in FIG. 4, the body area network 10 includes a plurality of sensor devices 100. The plurality of sensor device 100 of the body area network 10 may include implantable medical devices 102 implanted within a user and/or body worn devices 104 worn by the user. The body area network 10 may be used to monitor and/or treat the user. The plurality of sensor devices 100 may be used to periodically take vital readings (e.g., heart rate, blood pressure, etc.) throughout and about the user's body. Each of the sensor devices 100 may communicate with the others to pass relevant data between the sensor devices 100 to better monitor and/or remotely treat a user of the sensor devices 100. The sensor devices 100 may be programmed via at least one of the portable device 200 and the programmer 400. For example, the programmer 400 may be used to program the implantable medical devices 102, while the portable device 200 may be used to program the body worn devices 104.

The portable device 200 may act like a data collector or hub in which encrypted data is compiled (i.e., aggregated, etc.) in an efficient manner and send the data to the remote server 300 for decryption and processing. The remote server 300 may provide commands to the sensor devices 100 via the portable device 200 to provide treatments to the user or notify a healthcare professional. For example, an implantable medical device 102 may be configured to apply an anesthetic injection or release in a target area before a second implantable medical device 102 applies a shock to the target area (i.e., to reduce pain, etc.). In another example, the body area network 10 may be used to treat heart failure where multiple sensor devices 100 are used monitor, communicate, and treat different parameters related to heart failure. In yet another example, a sensor device 100 may be used to monitor the heart rate of a user for arrhythmias. In the presences of an arrhythmia, the same sensor device 100 or another sensor device 100 (such as a pacemaker) may automatically begin to regulate the heart or receive a command from the remote server 300 to begin regulating the heart.

Figure 5:
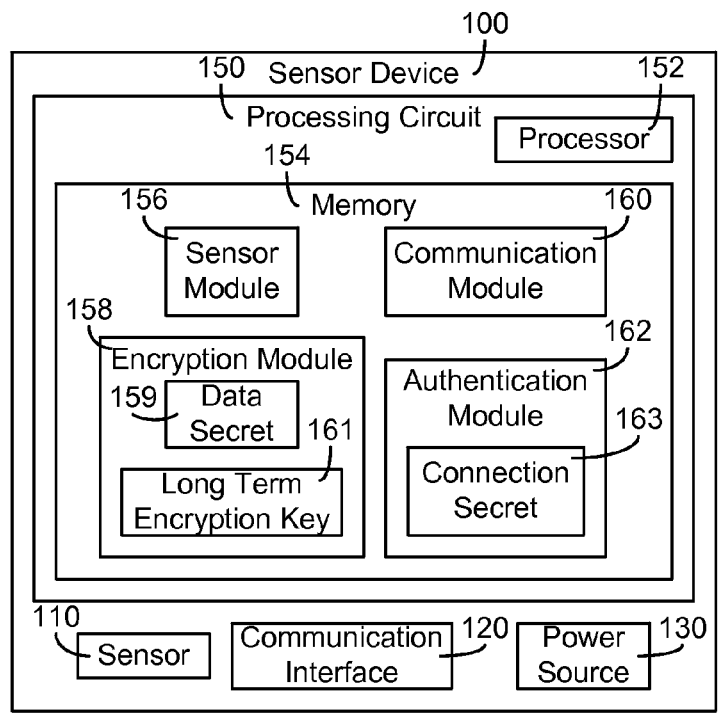
FIG. 5 is a block diagram of components of a sensor device, according to an exemplary embodiment.

Referring now to FIG. 5, the sensor device 100 includes a sensor 110, a communication interface 120, a power source 130, and a processing circuit 150. According to an exemplary embodiment, the sensor 110 is configured to acquire physiological data (e.g., a heart rate, a blood pressure, a body temperature, a respiratory rate, vital signs, etc.). The physiological data may be related to or used for indicating the health and/or activity of the patient (e.g., in a holistic manner, etc.). For example, the physiological data may indicate when a user of the sensor device 100 is resting, sitting, walking, running, etc. In another example, the physiological data may indicate when the user is sick, in pain, encountering a medical complication, healthy, etc. Sensor 110 may alternatively or additionally be configured to measure physiological data for a specific health treatment or measurement. For example, sensor 110 may measure blood sugar levels for treatment of diabetes, may measure heart activity for treatment in conjunction with a pacemaker or other system included in sensor device 100 or separately implanted in the user, and/or otherwise be used for treatment or measurement related to specific medical conditions. In another embodiment, the sensor 110 is configured to acquire device data indicating characteristics regarding the operation of the sensor device 100 (e.g., a battery level, a connection strength, etc.). The sensor 110 may be or include, but is not limited to, an accelerometer, a gyroscope, a heart rate sensor, a temperature sensor, and/or a blood pressure sensor, among other possibilities. In one embodiment, the sensor 110 is configured to monitor the health and/or activity of the user of the sensor device 100 over time. In some embodiments, the sensor device 100 includes a plurality of sensors 110, each configured to monitor different characteristics regarding the health and activity of the user.

Referring still to FIG. 5, the communication interface 120 may be configured to facilitate the communication between the sensor device 100 and at least one of the portable device 200, the remote server 300, and the programmer 400. In some embodiments, the communication interface facilitates the communication between a plurality of sensor devices 100 worn by or implanted within the user. The communication may be via any number of wired or wireless connections. For example, a wired connection may include a serial cable, a fiber optic cable, a CAT5 cable, or any other form of wired connection. A wireless connection may include the Internet, Wi-Fi, cellular, radio, Bluetooth, etc. In one embodiment, a controller area network (CAN) bus provides the exchange of signals, information, and/or data. The CAN bus includes any number of wired and wireless connections. The power source 130 is configured to power the sensor device 100. In one embodiment, the power source 130 is an internal power source, such as a battery. In some embodiments, the battery may be rechargeable. In other embodiments, the power source is an external power source.

As shown in FIG. 5, the processing circuit 150 includes a processor 152 and a memory 154. The processor 152 may be implemented as a general-purpose processor, an application specific integrated circuit (ASIC), one or more field programmable gate arrays (FPGAs), a digital signal processor (DSP), a group of processing components, or other suitable electronic processing components. One or more memory devices 154 (e.g., RAM, ROM, Flash Memory, hard disk storage, etc.) may store data and/or computer code for facilitating the various processes described herein. Thus, the one or more memory devices 154 may be communicably connected to the processor 152 and provide computer code or instructions to the processor 152 for executing the processes described in regard to the sensor device 100 herein. Moreover, the one or more memory devices 154 may be or include tangible, non-transient volatile memory or non-volatile memory. In some embodiments, the one or more memory devices 154 may include database components, object code components, script components, or any other type of information structure for supporting the various activities and information structures described herein.

The memory 154 is shown to include various modules for completing processes described herein. More particularly, the memory 154 includes modules configured to acquire and encrypt physiological data for processing by the remote server 300. While various modules with particular functionality are shown in FIG. 1, it will be understood that the sensor device 100 and the memory 154 may include any number of modules for completing the functions described herein. For example, the activities of multiple modules may be combined as a single module and additional modules with additional functionality may be included. Further, it will be understood that the processing circuit 150 of the sensor device 100 may further control other processes beyond the scope of the present disclosure.

As shown in FIG. 5, the sensor device 100 includes a sensor module 156, an encryption module 158, a communication module 160, and an authentication module 162. The sensor module 156 may be communicably coupled to the sensor 110 and configured to receive the acquired physiological data and/or device data from the sensor 110. The encryption module 158 is configured to encrypt the data received by the sensor module 156. According to an exemplary embodiment, the encryption module 158 is configured to encrypt the data with a data secret 159. As is described more fully herein, the data secret 159 may be based on user credentials (e.g., name, identification number, username, password, serial number, etc.). In one embodiment, the data secret 159 is predefined within the encryption module 158 by the programmer 400 or at the time of manufacture. In some embodiments, the encryption module 158 is configured to perform a double encryption of the data, first with the data secret 159 for a first layer of encryption, and second with a long term encryption key 161 for a second layer of encryption. In one embodiment, the sensor device 100 determines the long term encryption key 161 during an authentication process with the portable device 200, which is described more fully herein with reference to FIGS. 8A-11. In another embodiment, the encryption module 158 encrypts the data with a connection secret 163 to provide a first, second, or third layer of encryption to the data.

The authentication module 162 is configured to authenticate a connection between the sensor device 100 and the portable device 200. In one embodiment, the authentication process includes using a connection secret 163. As is described more fully herein, the connection secret 163 may be based on the user credentials (e.g., name, identification number, etc.) of the user of the sensor device 100. In one embodiment, the connection secret 163 is predefined within the encryption module 158 by the programmer 400 or at the time of manufacture. The connection secret 163 may be compared to a connection secret stored in the remote server 300 and acquired by the portable device 200 to initiate the authentication process. The communication module 160 may be communicably coupled to the communication interface 120 and configured to control the communication between the sensor device 100 and at least one of the portable device 200, the remote server 300, and the programmer 400. In one embodiment, the communication module 160 controls the transfer of the acquired data from the sensor device 100 to the portable device 200 and/or the remote server 300. In other embodiments, the communication module 160 receives the data secret 159 and the connection secret 163 from the programmer 400. In other embodiments, the communication module 160 receives a connection question from the portable device 200 to initiate the authentication/pairing process.

Figure 6:
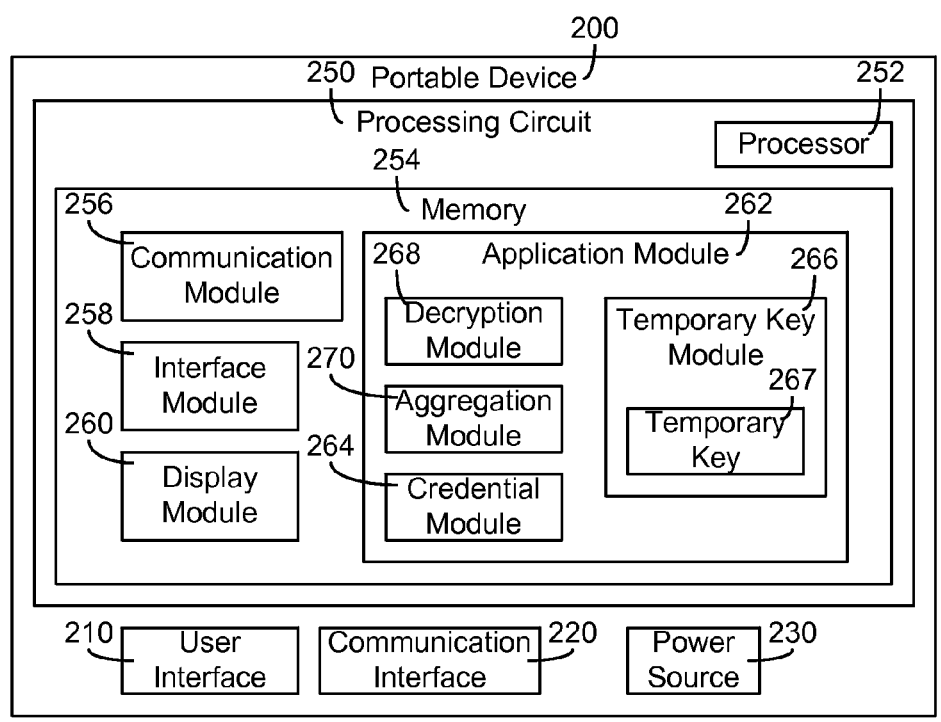
FIG. 6 is a block diagram of components of a user device, according to an exemplary embodiment.

Referring now to FIG. 6, the portable device 200 includes a user interface 210, a communication interface 220, a power source 230, and a processing circuit 250. According to an exemplary embodiment, the user interface 210 is configured to provide a display to the user of the sensor device 100. In one embodiment, the display includes processed data (e.g., processed by the remote server 300, etc.) indicating the health and/or activity of the patient (e.g., in a holistic manner, a summarized manner, etc.). For example, the physiological data may be provided in an organized chart or graph providing information over a time period or during different activities. The user may have the ability to sort or select specific portions of the processed data to obtain a closer look or a more thorough analysis. In another embodiment, the display includes a login interface where the user of the sensor device 100 may enter his/her user credentials (e.g., name, identification number, etc.). In further embodiments, the user interface 210 provides the user with an indication of the charge level of the power source 230 of the portable device 200 and/or the power source 130 of the sensor device 100. The user interface 210 may include a display screen, a touch screen, one or more buttons, a touch pad, a mouse, and/or other devices to allow a user to operate the portable device 200. The power source 230 is configured to power the portable device 200. In one embodiment, the power source 230 is an internal power source, such as a battery. In some embodiments, the battery may be rechargeable. In other embodiments, the power source 230 is an external power source (e.g., provided through a cable connecting to mains power, a wall outlet, etc.).

Referring still to FIG. 6, the communication interface 220 may be configured to facilitate the communication between the portable device 200 and at least one of the sensor device 100 and the remote server 300. The communication may be via any number of wired or wireless connections. For example, a wired connection may include a serial cable, a fiber optic cable, a CAT5 cable, or any other form of wired connection. In comparison, a wireless connection may include the Internet, Wi-Fi, cellular, radio, Bluetooth, etc. In one embodiment, a controller area network (CAN) bus provides the exchange of signals, information, and/or data. The CAN bus includes any number of wired and wireless connections.

As shown in FIG. 6, the processing circuit 250 includes a processor 252 and a memory 254. The processor 252 may be implemented as a general-purpose processor, an application specific integrated circuit (ASIC), one or more field programmable gate arrays (FPGAs), a digital signal processor (DSP), a group of processing components, or other suitable electronic processing components. One or more memory devices 254 (e.g., RAM, ROM, Flash Memory, hard disk storage, etc.) may store data and/or computer code for facilitating the various processes described herein. Thus, the one or more memory devices 254 may be communicably connected to the processor 252 and provide computer code or instructions to the processor 252 for executing the processes described in regard to the portable device 200 herein. Moreover, the one or more memory devices 254 may be or include tangible, non-transient volatile memory or non-volatile memory. In some embodiments, the one or more memory devices 254 may include database components, object code components, script components, or any other type of information structure for supporting the various activities and information structures described herein.

The memory 254 is shown to include various modules for completing processes described herein. More particularly, the memory 254 includes modules configured establish a secure connection between the sensor device 100 and the remote server 300, and to provide the user with a display of the processed data acquired by the sensor device 100 and processed by the remote server 300. While various modules with particular functionality are shown in FIG. 2, it will be understood that the portable device 200 and the memory 254 may include any number of modules for completing the functions described herein. For example, the activities of multiple modules may be combined as a single module and additional modules with additional functionality may be included. Further, it will be understood that the processing circuit 250 of the portable device 200 may further control other processes beyond the scope of the present disclosure.

As shown in FIG. 6, the portable device 200 includes a communication module 256, an interface module 258, a display module 260, and an application module 262. The application module 262 includes a credential module 264, a temporary key module 266, a decryption module 268, and an aggregation module 270. The application module 262 is configured to provide the user with an interface (e.g., an application interface, etc.) to access at least one of the sensor device 100 and the remote server 300 such that the user may monitor their health and activity (e.g., indicated by processed physiological data, etc.). The interface module 258 may be configured to receive an input from a user of the portable device 200 via the user interface 210 (e.g., touchscreen inputs, button inputs, etc.). The input may include a command to operate the portable device 200 (e.g., turn on, turn off, select a feature, etc.). The input may also include a command to open the application interface provided by the application module 262 specific to the sensor device 100. During initial configuration or setup, the credential module 264 may provide a user interface such that the user may enter his/her user credential information (e.g., name, identification number, username, password, serial number, etc.). In some embodiments, the user credentials must be entered each time the user accesses the application. The display module 260 is configured to display the application for accessing the sensor device 100 and/or the remote sever 300, as well as processed data. The display module 260 may also be configured to display various other features and/or applications not related to the present disclosure.

The communication module 256 may be communicably coupled to the communication interface 220 and configured to control the communication between the portable device 200 and at least one of the sensor device 100 and the remote server 300. In one embodiment, the communication module 256 controls the transfer of the user credentials from the portable device 200 to the remote server 300 to acquire a connection secret (e.g., connection secret 363 of FIG. 3, etc.) associated with the connection secret 163 of the sensor device 100 (e.g., based on the user credentials, etc.). The communication module 256 may communicate the connection secret or a connection question derived from the connection secret to the sensor device 100 to start the authentication process (mention above) and pair (e.g., create a connection between, etc.) the portable device 200 and the sensor device 100. The temporary key module 266 may provide a temporary key 267 to the sensor device 100 (e.g., via the communication module 256, etc.) to generate the long term encryption key 161 to establish a secure connection between the portable device 200 and the sensor device 100. With a secure connection established, the portable device 200 may receive the double encrypted physiological data and/or device data from the sensor device 100 (e.g., encrypted by the long term encryption key 161 and the data secret 159, etc.). The decryption module 268 may perform a first decryption on the double encrypted data using the long term encryption key 161 determined jointly by the sensor device 100 and the portable device 200. The communication module 256 may then send single decrypted data to the remote server 300 for a second decryption and data analysis. As is described more fully herein, the remote server 300 is configured to analyze the decrypted data and send the processed data to the portable device to be displayed via the display module 260 on the user interface 210 of the portable device 200.

In some embodiments, the portable device 200 may be connected to a plurality of sensor devices 100 of a user creating a body area network (e.g., the body area network 10, etc.). In this case, the aggregation module 270 may be configured to aggregate the single encrypted data from the plurality of sensor devices 100 to be provided to the remote server 300. The aggregation module 270 may also be configured to receive the processed data from the remote server 300 for each of the sensor devices 100, and display the data via display module 260 in a concise, easy to read format (e.g., separated by device, in a table, in a graph/chart, etc.).

Figure 7:
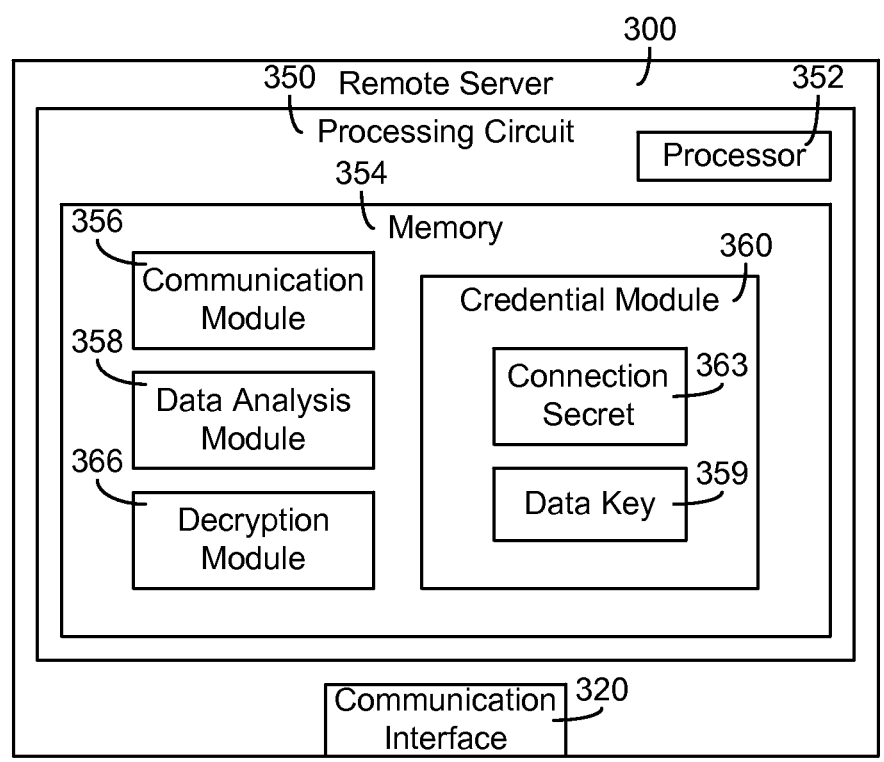
FIG. 7 is a block diagram of components of a remote server, according to an exemplary embodiment.

Referring now to FIG. 7, the remote server 300 includes a communication interface 320 and a processing circuit 350. The communication interface 320 may be configured to facilitate the communication between the remote server 300 and at least one of the portable device 200 and the programmer 400. The communication may be via any number of wired or wireless connections. For example, a wired connection may include a serial cable, a fiber optic cable, a CAT5 cable, or any other form of wired connection. In comparison, a wireless connection may include the Internet, Wi-Fi, cellular, radio, Bluetooth, etc. In one embodiment, a controller area network (CAN) bus provides the exchange of signals, information, and/or data. The CAN bus includes any number of wired and wireless connections.

As shown in FIG. 7, the processing circuit 350 includes a processor 352 and a memory 354. The processor 352 may be implemented as a general-purpose processor, an application specific integrated circuit (ASIC), one or more field programmable gate arrays (FPGAs), a digital signal processor (DSP), a group of processing components, or other suitable electronic processing components. One or more memory devices 354 (e.g., RAM, ROM, Flash Memory, hard disk storage, etc.) may store data and/or computer code for facilitating the various processes described herein. Thus, the one or more memory devices 354 may be communicably connected to the processor 352 and provide computer code or instructions to the processor 352 for executing the processes described in regard to the remote server 300 herein. Moreover, the one or more memory devices 354 may be or include tangible, non-transient volatile memory or non-volatile memory. In some embodiments, the one or more memory devices 354 may include database components, object code components, script components, or any other type of information structure for supporting the various activities and information structures described herein.

The memory 354 is shown to include various modules for completing processes described herein. More particularly, the memory 354 includes modules configured to receive and analyze data for a plurality of sensor devices 100. While various modules with particular functionality are shown in FIG. 3, it will be understood that the remote server 300 and the memory 354 may include any number of modules for completing the functions described herein. For example, the activities of multiple modules may be combined as a single module and additional modules with additional functionality may be included. Further, it will be understood that the processing circuit 350 of the remote server 300 may further control other processes beyond the scope of the present disclosure.

As shown in FIG. 7, the remote server 300 includes a communication module 356, a data analysis module 358, a credential module 360, and a decryption module 366. The communication module 256 may be communicably coupled to the communication interface 320 and configured to control the communication between the remote server 300 and at least one of the portable device 200 and the programmer 400. In one embodiment, the communication module 356 receives a data key 359, a connection secret 363, and user credentials from the programmer 400 for each user of one of the plurality of sensor devices 100. The data key 359 and the connection secret 363 may be stored in the credential module 360 for each sensor device 100 based on the user credentials to register the sensor devices 100. The data key 359 and the connection secret 363 uniquely correspond with the data secret 159 and the connection secret 163 stored on an individual sensor device 100 (e.g., based on the user credentials, etc.). Therefore, each of the data keys 359, the connection secrets 363, the data secrets 159, and the connection secrets 163 are unique for each sensor device 100 and user of the sensor device 100. According to an exemplary embodiment, the connection secret 363 and the connection secret 163 are identical. The communication module 356 may also be configured to receive user credentials from the portable device 200 as a request to receive the connection secret 363 for one of the plurality of sensor devices 100. In turn, the credential module 360 determines the connection secret 363 that corresponds with the provided user credentials and the connection secret 363 is transmitted to the portable device 200 that made the request. In further embodiments, the communication module 356 is configured to receive the single decrypted data (e.g., single decrypted physiological data, etc.) from the portable device 200.

The decryption module 366 is configured to perform a decryption process (e.g., a second decryption, etc.) on the single encrypted data using the data key 359 stored in the credential module 360 corresponding to the designated user credentials and the associated sensor device 100. The data key 359 is associated with the data secret 159 of the sensor device 100, and therefore facilitates the final decryption of the physiological data and/or device data acquired by the sensor device 100. According to an exemplary embodiment, the remote server 300 is the only component of the communication system that has access to raw data acquired by the sensor device 100 (i.e., the portable device 200 does not have access to raw data, etc.). The sensor device 100 may acquire raw data via sensor 110, encrypt the raw data using the double encryption described herein, and transmit the raw data to remote server 300 via portable device 200. According to an exemplary embodiment, the portable device 200 does not decrypt both layers of the double encryption, and therefore the portable device 200 may not have access to the raw data acquired by sensor device 100. In some embodiments, the portable device 200 decrypts a single layer of encryption with the remote server 300 decrypting the final layer of encryption. In other embodiments, the decryption module 366 decrypts both layers of encryption with the first layer of encryption used in additional communication between remote server 300 and portable device 200 (e.g., in transmitting analyzed physiological data, a summary of physiological data, a report, or other information other than raw physiological data to portable device 200 from remote server 300).

The data analysis module 358 is configured to receive and analyze the decrypted physiological and/or device data and process the decrypted data. Analyzing the decrypted data may include compiling data over time in order to determine daily, weekly, and/or monthly trends of the user of the sensor device 100 based on the physiological data. For example, the data analysis module 358 may determine a trend in heart rate each day based on a user's daily routine. Analyzing the data may also include removing data that indicates some sort of anomaly or error in the data. In one embodiment, the data analysis module 358 triggers a warning or a notification message which may be sent by the communication module 356 to the portable device 200 if the data begins to deviate from the trends. In another embodiment, the data analysis module 358 informs a healthcare provider (e.g., the user's doctor, the nearest hospital, etc.) via the communication module 356 if the analyzed data indicates that the user of the sensor device 100 may require medical attention. According to an exemplary embodiment, a summary of the analyzed/processed data is sent to the portable device 200. In one embodiment, the summary data is sent to the portable device 200 upon request from the user (e.g., via the application user interface, etc.). In other embodiments, the portable device 200 receives regular, schedule updates (e.g., hourly, daily, weekly, etc.). In another embodiment, the portable device 200 receives "push" notifications from the remote server 300 regarding updates to the data or changes in the user's trends. The summary data may include data regarding medical device status and health trends of the user based on the physiological and device data.

Figure 8A:
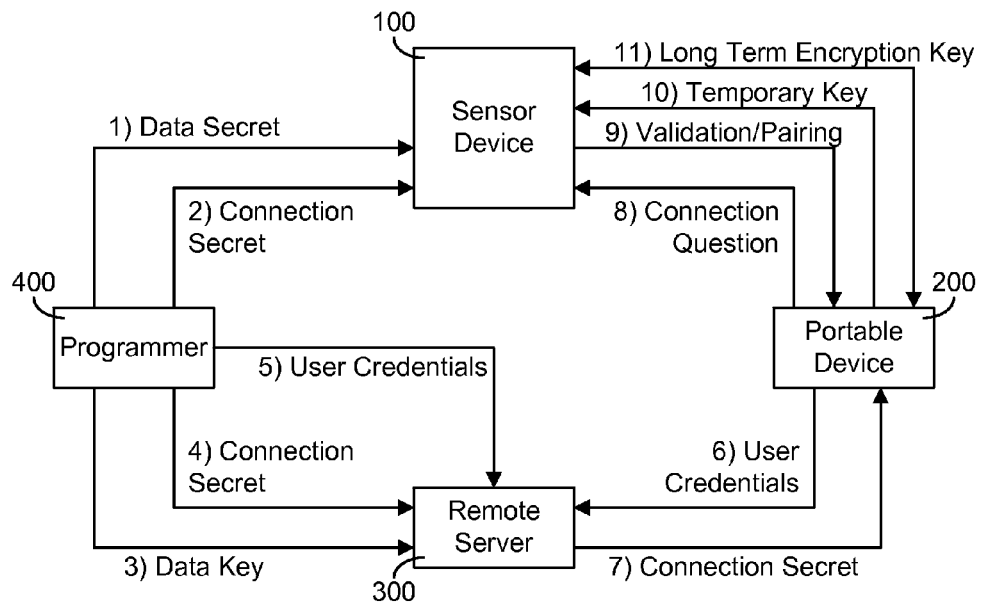
FIG. 8A is a schematic diagram of an authentication process between a sensor device and a user device, according to an exemplary embodiment.

Referring now to FIG. 8A, a schematic diagram of an authentication and pairing process between the sensor device 100 and the portable device 200 is shown according to an exemplary embodiment. The programmer 400 (e.g., an authority computer, a secure device, a programming device, etc.) receives user credentials (e.g., username, password, serial number, identification number, etc.) from an authority user for a user of a particular sensor device 100. The authority user may be the manufacturer of the sensor device 100, a retailer selling the sensor device 100, a healthcare provider implanting or assigning the sensor device 100 to the user (e.g., a patient, etc.), or the end user of the sensor device 100 itself. The programmer 400 is configured to assign and upload (1) a data secret (e.g., the data secret 159, etc.) and (2) a connection secret (e.g., the connection secret 163, etc.) to the sensor device 100 unique to the user credentials. The programmer is further configured to upload (3) a data key (e.g., the data key 359, etc.) and (4) a connection secret (e.g., the connection secret 363, etc.), along with (5) the user credentials to the remote server 300, associated with the data secret and connection secret of the sensor device 100. In one embodiment, the connection secret uploaded to the remote server 300 is identical to the connection secret programmed in the sensor device 100.

The user of the sensor device 100 may then connect to the sensor device 100 and the remote server 300 via the portable device 200. By way of example, the user may download an application for the sensor device 100 from an application store. The application may provide a user interface that allows for a user to connect to the sensor device 100 and remote server 300 by entering (6) the user credentials for the user and associated with the connection secret of the sensor device 100. By way of another example, the user may access a user interface to enter in the user credentials to connect to the sensor device 100 and remote server 300 via a website on the Internet. The remote server 300 receives the user credentials from the portable device 200 and in turn sends (7) the connection secret associated with the received user credentials to the portable device 200. The portable device 200 then initiates an authentication process by sending (8) a connection question to the sensor device 100. In one embodiment, the connection question is created using one or more transformation functions on the connection secret received from the remote server 300 or otherwise constructed from the connection secret. According to an exemplary embodiment, the portable device 200 derives the connection question. In another embodiment, the portable device 200 receives the connection question from the remote server 300.

The sensor device 100 in turn performs (9) a validation process to facilitate the pairing of the sensor device 100 and portable device 100. In one embodiment, the sensor device 100 compares the connection secret stored in its memory to the connection question received from the portable device 200 to validate the portable device 200. In other embodiments, the sensor device 100 decrypts the connection question with the connection secret or applies a reverse algorithm to validate the portable device 200. Once validated, the portable device 200 starts the pairing by sending (10) a temporary key (e.g., the temporary key 267, etc.) to the sensor device 100. The portable device 200 and the sensor device 100 establish a secure connection with (11) a long term encryption key (e.g., the long term encryption key 161, etc.) generated via the combination of the temporary key and the connection secret. The long term encryption key facilitates the transfer of sensitive information in an encrypted form (e.g., since the long term encryption key is only known by the sensor device 100 and the portable device 200, etc.). According to an exemplary embodiment, the portable device 200 is constantly connected to the remote server 300 during the authentication process such that if a connection between the two is lost, the portable device 200 is unable to communicate with the sensor device 100. In one embodiment, the user credentials are not stored on the portable device 200 such that unauthorized users may not communicate with the sensor device 100 or the remote server 300. According to an exemplary embodiment, the portable device 200 does not have access to the data key stored in the remote server 300.

Figure 8B:
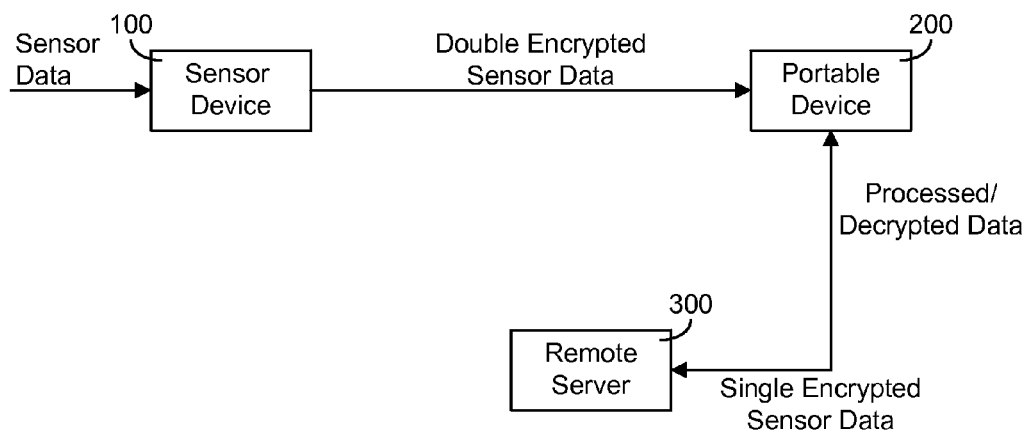
FIG. 8B is a schematic diagram of a data encryption and analysis process, according to an exemplary embodiment.

Referring now to FIG. 8B, a schematic diagram of a data encryption and analysis process is shown according to an exemplary embodiment. As described above, the sensor device 100 includes sensors 110 configured to acquire data (e.g., physiological data, device data, etc.) regarding at least one of the user and the sensor device 100. The sensor device 100 encrypts the sensor data with the data secret and the long term encryption key and sends the double encrypted sensor data to the portable device 200 (e.g., periodically, upon request by the user, etc.). In an alternative embodiment, the sensor device 100 does not encrypt the sensor data with both the long term encryption key and the data secret. In another alternative embodiment, the sensor device 100 encrypts a first portion of the sensor data with two layers of encryption (e.g., with both the long term encryption key and the data secret, etc.) and a second portion of the sensor data with one layer of encryption (e.g., with the long term encryption key, etc.). Therefore, the portable device 200 may be able to display the second portion of the sensor data to the user without having to be sent to the remote server 300.

According to an exemplary embodiment, the portable device 200 performs a first decryption process to remove the long term encryption key from the double encrypted sensor data. The portable device 200 sends the single encrypted sensor data to the remote server 300 for a final decryption process (e.g., a second decryption process, a first decryption process in some instances, etc.). The remote server 300 decrypts the single encrypted sensor data by removing the data secret with the corresponding data key. The remote server 300 may then process the decrypted sensor data and send the processed data (e.g., a summary, etc.) to the portable device 200 for the user to view. In an alternative embodiment, the portable device 200 receives single encrypted sensor data, and therefore does not perform a decryption process. In other embodiments, the portable device 200 receives single encrypted sensor data and/or double encrypted sensor data from the sensor device 100. The portable device 200 may perform a decryption of at least one of the single encrypted sensor data and the double encrypted sensor data. Therefore, the portable device 200 may be able to display specific data to a user of the portable device 200 directly from data received from the sensor device 100, as well as transmit other data to the remote server 300 for further decryption and processing. In some embodiments, the sensor device 100 itself is configured to display data to the user (e.g., a smart watch, a body worn sensor device with a display, etc.). In a further alternative embodiment, the portable device 200 does not perform a first decryption process but rather sends double encrypted sensor data (e.g., physiological data) to remote server 300. The remote server 300 decrypts both layers of encryption using the connection secret and data key. The remote server 300 may encrypt further communications (e.g., transmissions of data summaries, reports, or other information other than raw sensor data, etc.) with the portable device 200 using the connection secret or other encryption. The portable device 200 may decrypt transmissions from the remote server 300 using the connection secret or other key.

According to another exemplary embodiment, software and/or software updates may be downloaded from the remote server 300 to the portable device 200. The software and/or software updates may then be used to update the sensor device 100 and/or adjust settings of the sensor device 100. In some embodiments, the software may reside on the remote server 300 from where specific commands may be sent to the portable device 200 to update and/or adjust settings of the sensor device 100.

Figure 9:
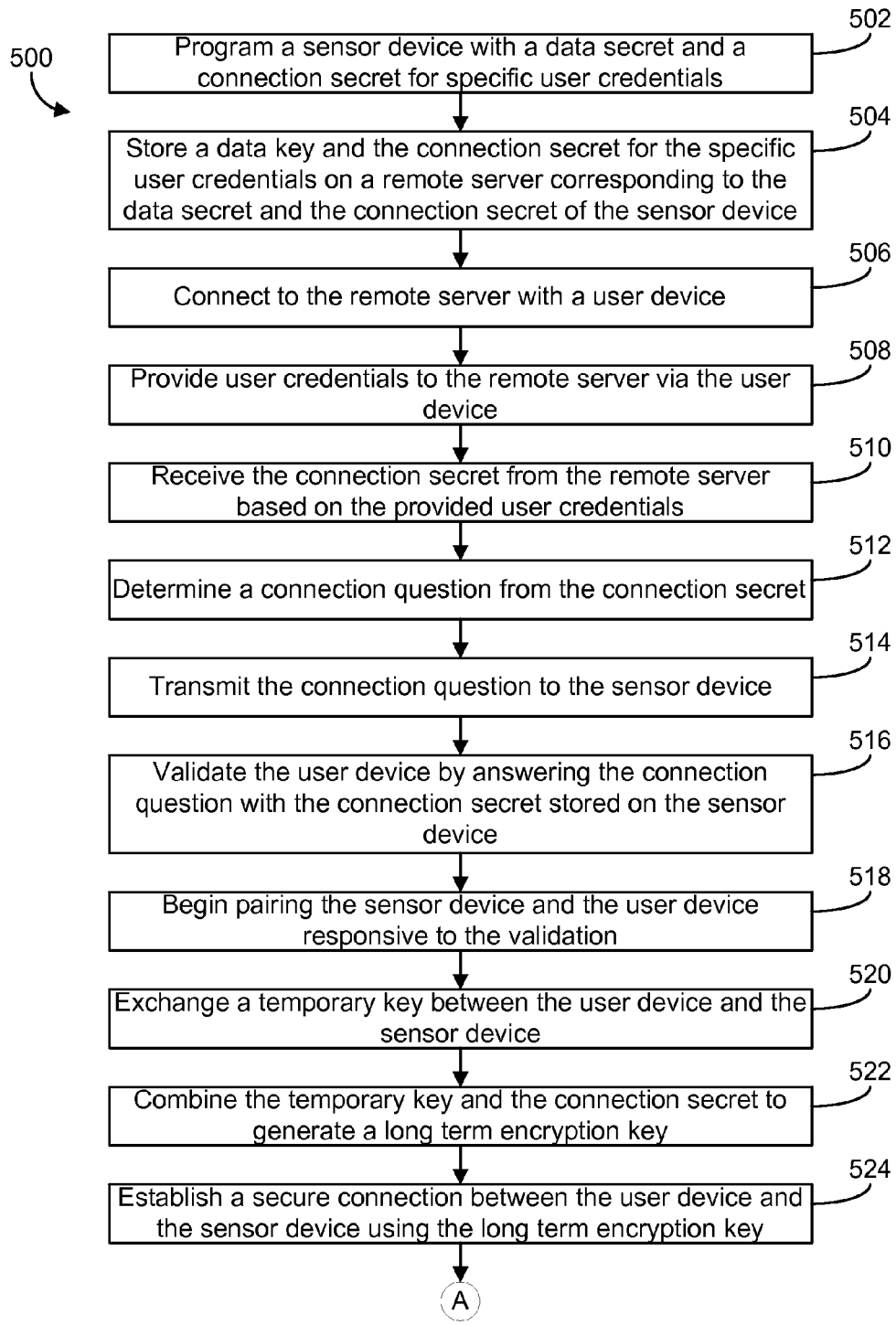
FIG. 9 is a flow diagram of a method for authenticating a connection between a sensor device and a user device, according to an exemplary embodiment.

Referring now to FIG. 9, a method 500 for authenticating a connection between a sensor device and a portable device is shown according to an exemplary embodiment. In one example embodiment, method 500 may be implemented with the communication system of FIGS. 1-8B. Accordingly, method 500 may be described in regard to FIGS. 1-8B.

At step 502, a programmer (e.g., the programmer 400, etc.) programs a sensor device (e.g., the sensor device 100, etc.) with a data secret and a connection secret based on specific user credentials. At step 504, the programmer stores (e.g., uploads, etc.) a data key and the connection secret for the specific user credentials on a remote server corresponding to the data secret and the connection secret of the sensor device (i.e., registering the sensor device on the remote server, etc.). At 506, a user connects to a remote server with a user device (e.g., the portable device 200, a stationary device, etc.). At step 508, the user provides his/her user credentials to the remote server with the user device. By way of example, the user device may include an application that provides a user interface for the user to enter the user credentials. By way of another example, the user may access a website via the user device that provides a user interface for the user to enter the user credentials. The remote server determines the connection secret that corresponds with the provided user credentials and sends the connection secret to the user device.

At step 510, the user device receives the connection secret from the remote server based on the provided user credentials. At step 512, the user device determines a connection question from the connection secret received from the remote server. At step 514, the user device transmits the connection question to the sensor device. At step 516, the sensor device validates the user device by answering/decrypting the connection question using the connection secret stored on the sensor device. If the sensor device validates the user device, at step 518, the sensor device and the user device being pairing. If the connection between the two is determined to be invalid, the sensor device denies the user device access to data (e.g., encrypted data, etc.) stored on the sensor device. At step 520, the user device sends a temporary key to the sensor device. The temporary key may be a random number generated by the user device, some sort of identifier for the user device, or another type of key only known by the user device prior to being sent to the sensor device. At step 522, the sensor device and the user device combine the temporary key with the connection secret (e.g., known by both, etc.) to generate a long term encryption key. At step 524, the sensor device and the user device establish a secure connection using the long term encryption key. With the secure connection, the sensor device may transmit encrypted data to the user device to be sent to the remote server for processing.

Figure 10:
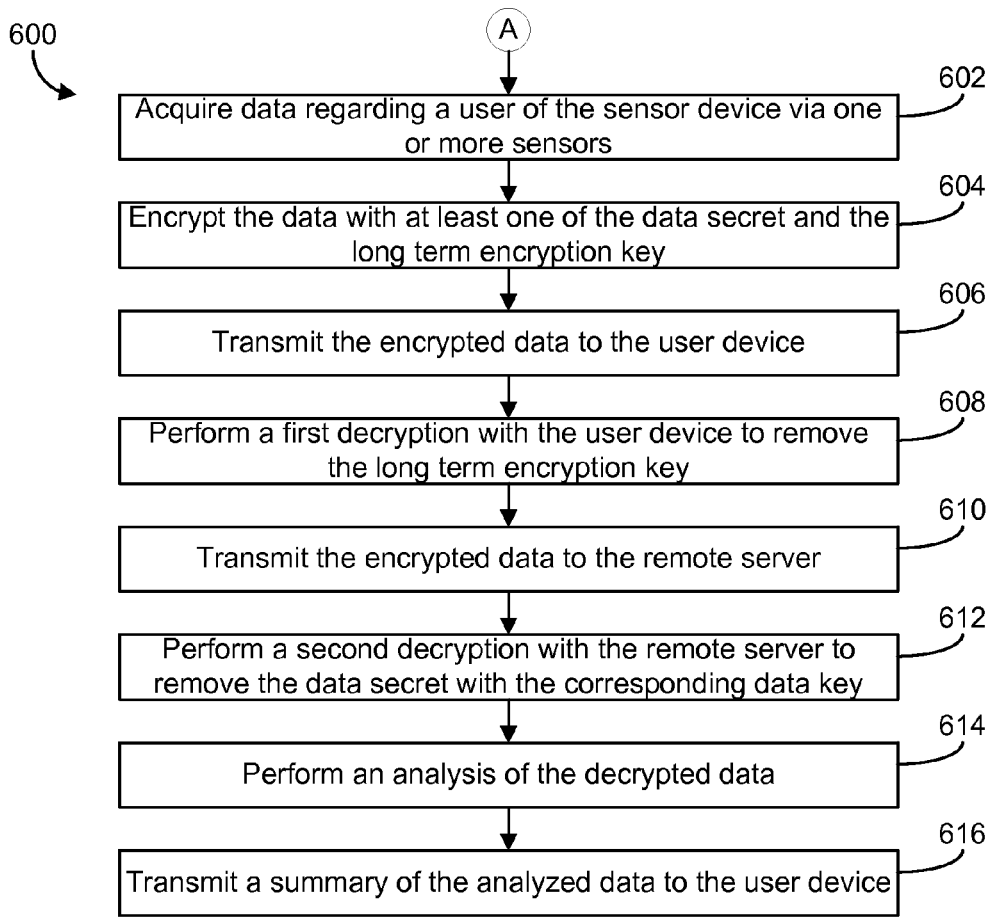
FIG. 10 is a flow diagram of a method of encrypting and analyzing data acquired by a sensor device, according to an exemplary embodiment.

Referring now to FIG. 10, a method 600 of encrypting and analyzing data acquired by a sensor device is shown according to an exemplary embodiment. In one example embodiment, method 600 may be implemented with the communication system of FIGS. 1-8B. Accordingly, method 600 may be described in regard to FIGS. 1-8B.

Following the authentication of the user device and the establishment of a secure connection, the sensor device may transmit data to the remote server via the user device. At step 602, the sensor device acquires data via one or more sensors (e.g., the sensors 110, etc.). The data may include physiological data regarding the user and device data regarding the sensor device. At step 604, the sensor device encrypts the data with the data secret and/or the long term encryption key (e.g., double encrypted data, single encrypted data, etc.). At step 606, the sensor device transmits the encrypted data to the user device. At step 608, the user device performs a first decryption process to remove the long term encryption key.

In some embodiments, step 608 is omitted if the sensor device does not encrypt the data with the long term encryption key (e.g., a single encryption, etc.). At step 610, the user device transmits the encrypted data (e.g., single encrypted data, etc.) to the remote server.

At step 612, the remote server performs a decryption process (e.g., a second decryption process, etc.) to remove the data secret with the corresponding data key. In some embodiments, the remote server performs the only decryption of the encrypted data (e.g., if the data is not encrypted with the long term encryption key, etc.). In an alternate embodiment, the remote server decrypts multiple layers of encryption (e.g., two, etc.) with the connection secret and the data key that correspond with the connection secret and the data secret of the sensor device. At step 614, the remote server analyzes/processes the decrypted data. At step 616, the remote server transmits a summary of the analyzed data to the user device for the viewing by the user of the sensor device. In some embodiment, the remote server 300 encrypts the summary data with the connection secret before sending the summary data to the portable device. The portable device 200 may then decrypt the encrypted summary data using the connection secret previously received (e.g., at step 510, etc.) to provide the summary data to the user in a viewable form. In other embodiments, the remote server contacts or sends the data to the user's healthcare provider (e.g., the user's doctor, etc.). In an alternative embodiment, the remote server sends a command to the sensor device to take an action such as provide an injection, a shock, and the like to provide remote treatment to the user based on the data indicating such an action is needed.

In some embodiments, the methods 500 and 600 correspond with a plurality of sensor devices for an individual user device. For example, the sensor devices may create a body area network (e.g., the body area network 10, etc.) which includes any combination of implanted and worn sensor devices (e.g., the implantable medical device 102, body worn device 104, etc.). Each of the plurality of sensor devices may communicate with each other to better monitor and treat a user. A user device may act as a hub device which receives a plurality of data from the plurality of sensor devices. The user device may receive the plurality of data periodically (e.g., based on a schedule, etc.) or the user may request data from one or more of the plurality of sensor devices. The user device may aggregate the plurality of data in an efficient and organized manner to be sent to the remote server for processing. In other embodiments, the methods 500 and 600 correspond with a plurality of users of one or more sensor devices. For example, the remote sever may be communicably coupled to a plurality of user devices and configured to process and analyze data regarding a plurality of users and a plurality of sensor device.

Figure 11:
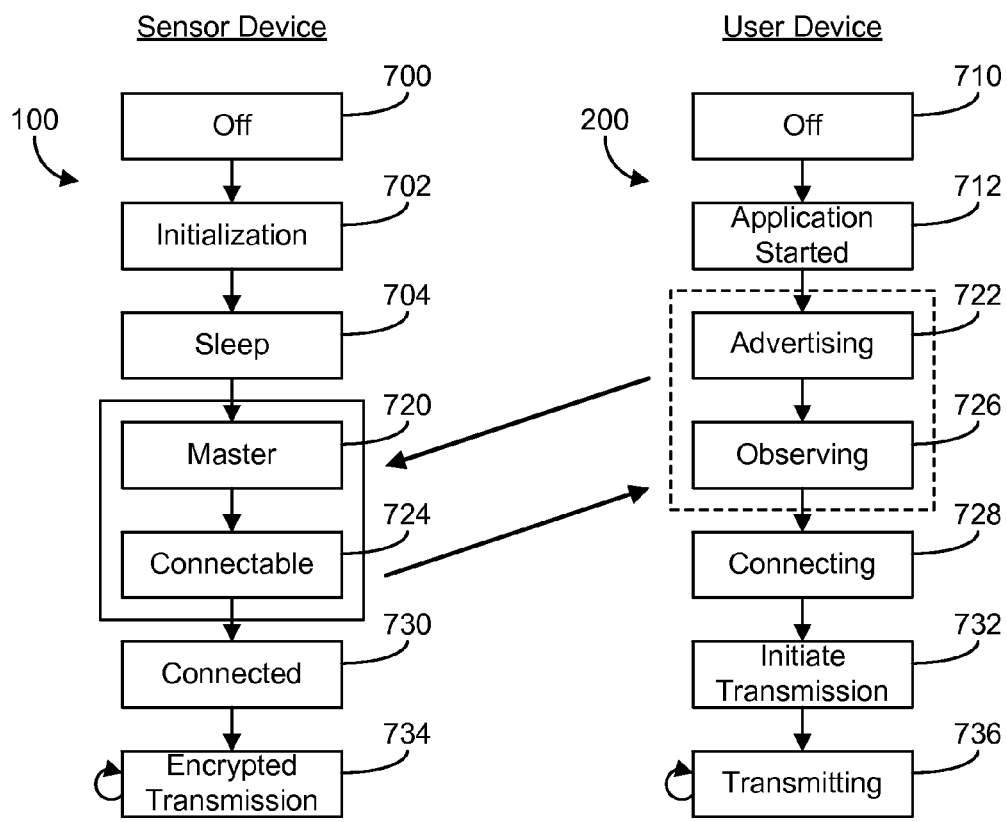
FIG. 11 is a block diagram illustrating an activation process for a sensor device, according to an exemplary embodiment.

Referring now to FIG. 11, the sensor device 100 may be configured to start up in a master mode. The sensor device 100 may then be activated through many means (e.g., physical proximity, timer based, etc.) where the sensor device 100 enters into a slave/listen mode. As shown in FIG. 7, the sensor device 100 starts in an off state 700. The sensor device 100 may be turned on and programmed during an initialization step 702. For example, the sensor device 100 may be turned on and programmed (e.g., via the programmer 400, etc.) based on the user credentials of a patient/user. Once initialized, the sensor device 100 may enter into a sleep state 704 (e.g., to conserve power, etc.) where the sensor device 100 acts as a master device 720, awaiting to be activated (e.g., via the portable device 200, etc.). While acting as a master device 720, the sensor device 100 may not exit the sleep state until a portable device 200 requests to pair with the sensor device 100 and has a valid connection secret. Therefore, the sensor device 100 has the ability of selective pairing when acting as the master device where it is configured to have the ability to decline the paring with portable devices 200 that have not been validated by the remote server 300 prior to the paring session (i.e., portable devices that do not have not connected to the remote server and received the connection secret, etc.).

Referring still to FIG. 11, the portable device 200 may start without being connected to the sensor device 100, where relative to the sensor device 100 the portable device 200 is essentially in an off state 710. A user (e.g., a patient with implantable sensor device 100, a user with a body worn sensor device 100, etc.) may open an application 712 on the portable device 200. The application 712 (or another user interface such as a website) allows the user to enter his/her user credentials to establish a connection with remote server 300 and in turn the sensor device 100 (e.g., via the connection secret 363, etc.). With valid user credentials, the portable device 200 receives the connection secret from the remote server 300 and may begin an advertising process 722 by sending a connection question to the sensor device 100 to initiate a pairing session between the portable device 200 and the sensor device 100. The portable device 200 may then begin observing (726) for a response from the sensor device 100.

Once the sensor device 100 hears from the portable device 200 with a valid connection secret, the sensor device 100 switches its role from acting as a master device 720 in the master mode to a slave device in a slave where it enters into a connectable state 724 and responds to the request/advertisement of the portable device 200 (e.g., if the connection secret 363 corresponds with the connection secret 163, etc.). The portable device 200 receives/observes the response from the sensor device 100 and begins a connection process 728 between the sensor device 100 and the portable device 200 (e.g., the sensor device 100 and the portable device 200 establish the long term encryption key 161, etc.). The sensor device 100 may then connect (730) to the portable device 200, finalizing the pairing process. This mechanism may allow both the sensor device 100 and the portable device 200 to find each other and authenticate each other prior to establishing a bi-directional communication session. The mechanism described above uniquely address a couple of items: (i) it enables secure communication between the sensor device 100 and the portable device 200 (i.e., the implant is not discoverable by any other instrument, non-approved device cannot establish a session with the implant, etc.), (ii) it conserves power in the sensor device 100 by not constantly having to transmit identification information and then listen for a response from a portable device 200.

With a secure connection established between the sensor device 100 and the portable device 200, data may be transmitted between the sensor device 100 and the portable device 200. According to the exemplary embodiment shown in FIG. 11, the portable device 200 sends a transmission command 732 to the sensor device 100. This may be performed due to a request from the user on the application/user interface or based on a predefined schedule (e.g., daily, weekly, etc.). The sensor device 100 receives the transmission command 732 and begins a transmission process to send data in an encrypted transmission 734. The portable device 200 then receives the encrypted transmission 734 and transmits (736) the data to the remote server 300. In some embodiments, the portable device 200 performs a decryption on the encrypted data (as described above) before transmitting the data to the remote server 300. In other embodiments, the sensor device 100 sends the encrypted transmission 734 without receiving a transmission command 732 from the portable device 200. In an alternative embodiment, the transmission command 732 is sent to the sensor device 100 responsive to a request from the remote server 300 through the portable device 200.

The present disclosure contemplates methods, systems, and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Although the figures may show a specific order of method steps, the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

While various aspects and embodiments have been disclosed herein, other aspects and embodiments will be apparent to those skilled in the art. The various aspects and embodiments disclosed herein are for purposes of illustration and are not intended to be limiting.

What is claimed is:

1. A medical monitoring and communication system for wireless communication between an implantable medical device, a mobile user device, and a remote server, comprising:
    a sensor device communicably coupled to the implantable medical device and configured to:
        default to a master mode prior to pairing with the mobile user device;
        listen for a request to connect from the mobile user device;
        refrain from communicating with the mobile user device responsive to the request to connect from the mobile user device being invalid; and
        switch to a slave mode to allow cooperative pairing with the mobile user device responsive to the request to connect from the mobile user device being valid;
    wherein the mobile user device facilitates communication between the sensor device and the remote server when the mobile user device and the sensor device are cooperatively paired; and
    wherein the sensor device is configured to acquire data regarding at least one of a user of the sensor device or the sensor device, wherein the sensor device is configured to encrypt at least a portion of the data with at least one layer of encryption.

2. The system of claim 1, wherein the sensor device includes at least one of an implantable medical device or a body worn device.

3. The system of claim 1, wherein the sensor device includes a plurality of sensor devices, wherein the plurality of sensor devices form a body area network.

4. The system of claim 1, wherein the sensor device includes a display, wherein the display is configured to provide a portion of the data directly to the user.

5. The system of claim 1, wherein the sensor device is configured to send data to the remote server via the mobile user device.

6. The system of claim 5, wherein the sensor device is configured to provide a command to the mobile user device to decrypt at least a portion of the data encrypted by the sensor device and provide the data to the user without sending the portion of the data to the remote server.

7. The system of claim 5, wherein the remote server is configured to analyze the data and at least one of (i) send a summary of the data to the mobile user device or (ii) alert a healthcare provider of the user responsive to the data indicating the user requires immediate attention.

8. The system of claim 5, wherein the sensor device is configured to receive a command from the remote server via the mobile user device to administer a treatment to the user based on the data.

9. The system of claim 1, wherein the sensor device is programmed with a data secret and a connection secret based on user credentials, and wherein the remote server is configured to store a data key and the connection secret based on the user credentials and corresponding to the data secret and the connection secret of the sensor device.

10. The system of claim 9, wherein the mobile user device is configured to receive the connection secret from the remote server responsive to the user entering the user credentials associated with the connection secret.

11. The system of claim 10, wherein the mobile user device and the sensor device establish a secure connection with an encryption key responsive to the connection secret of the mobile user device corresponding with the connection secret of the sensor device and indicating a valid connection request, wherein the encryption key is generated based on a combination of a temporary key and the connection secret.

12. The system of claim 11, wherein the sensor device is configured to encrypt the data with a first layer of encryption with the encryption key and a second layer of encryption with the data secret, wherein the mobile user device is configured to perform a first decryption of the data with the encryption key to remove the first layer of encryption and the remote server is configured to perform a second decryption of the data with the data key to remove the second layer of encryption.

13. The system of claim 1, wherein the sensor device is configured to receive a command from the mobile user device to adjust a setting of the sensor device, wherein the mobile user device is configured to receive at least one of software or a software update from the remote server to adjust the setting of the sensor device.

14. The system of claim 1, wherein the sensor device is configured to receive a command from the remote server via the mobile user device to adjust a setting of the sensor device.

15. A method for wireless communication between an implantable medical device, a mobile user device, and a remote server, comprising:
   providing a sensor device communicably coupled to the implantable medical device;
   acquiring, by the sensor device, data regarding at least one of a user of the sensor device or the sensor device;
   setting the sensor device to default to a master mode when not paired with the mobile user device;
   receiving, by the sensor device, a connection request from the mobile user device;
   determining, by the sensor device, whether the connection request is a valid request;
   refraining, by the sensor device, from communicating with the mobile user device responsive to the connection request being invalid; and
   switching, by the sensor device, to a slave mode and cooperatively pairing the mobile user device and the sensor device responsive to the connection request being valid;
   wherein the sensor device is configured to encrypt at least a portion of the data with at least one layer of encryption.

16. A method for wireless communication between an implantable medical device, a mobile user device, and a remote server, comprising:
   providing a sensor device communicably coupled to the implantable medical device;
   setting the sensor device to default to a master mode when not paired with the mobile user device;
   receiving, by the sensor device, a connection request from the mobile user device;
   determining, by the sensor device, whether the connection request is a valid request;
   refraining, by the sensor device, from communicating with the mobile user device responsive to the connection request being invalid;
   switching, by the sensor device, to a slave mode and cooperatively pairing the mobile user device and the sensor device responsive to the connection request being valid;
   programming the sensor device with a connection secret based on user credentials; and
   storing the connection secret based on the user credentials on the remote sever.

17. The method of claim 16, further comprising receiving, by the mobile user device, the connection secret from the remote server responsive to a user entering the user credentials associated with the connection secret.

18. The method of claim 17, further comprising establishing a secure connection with an encryption key responsive to the connection secret of the mobile user device corresponding with the connection secret of the sensor device and indicating a valid connection request, wherein the encryption key is generated based on a combination of a temporary key and the connection secret.

* * * * *